United States Patent [19]

Doss

[11] 4,189,685
[45] Feb. 19, 1980

[54] SELF-PROTECTING TRANSISTOR OSCILLATOR FOR TREATING ANIMAL TISSUES

[75] Inventor: James D. Doss, Los Alamos, N. Mex.

[73] Assignee: The United States of America as represented by the United States Department of Energy, Washington, D.C.

[21] Appl. No.: 886,378

[22] Filed: Mar. 14, 1978

[51] Int. Cl.$^2$ .................. A61B 17/38; A61N 1/32; H03B 5/04; H03B 5/12

[52] U.S. Cl. .................. 331/62; 128/422; 219/10.77; 331/66; 331/117 R

[58] Field of Search ... 128/2.1 P, 422, 303.13–303.19; 331/62, 117 R, 66; 361/179, 180, 181, 188, 203; 328/8; 219/10.77, 10.75, 69 G

[56] References Cited

U.S. PATENT DOCUMENTS

| | | | |
|---|---|---|---|
| 1,724,508 | 8/1929 | Nauth | 128/422 |
| 3,025,858 | 3/1962 | Browner | 128/422 |
| 3,042,908 | 7/1962 | Pearson | 331/65 |
| 3,288,905 | 11/1966 | Markowitz | 331/117 |
| 3,614,651 | 10/1971 | Pasquier | 128/2.1 |

FOREIGN PATENT DOCUMENTS 1173999  7/1964  Fed. Rep. of Germany ........... 128/422

OTHER PUBLICATIONS

QST, R. W. Gunderson, p. 36–37 Aug. 1961.

*Primary Examiner*—Siegfried Grimm
*Attorney, Agent, or Firm*—R. V. Lupo; Jerome B. Rockwood

[57] ABSTRACT

A transistor oscillator circuit wherein the load current applied to animal tissue treatment electrodes is fed back to the transistor. Removal of load is sensed to automatically remove feedback and stop oscillations. A thermistor on one treatment electrode senses temperature, and by means of a control circuit controls oscillator transistor current.

1 Claim, 3 Drawing Figures

SELF-PROTECTING TRANSISTOR OSCILLATOR FOR TREATING ANIMAL TISSUES

BACKGROUND OF THE INVENTION

The present invention relates to oscillator circuits and more particularly to a self-protecting transistor oscillator circuit.

In conventional transistor oscillator circuits, removal of the load from the oscillator increases the collector-to-emitter alternating voltage. This excess voltage can destroy the oscillating transistor. To avoid this problem, buffer circuits between the oscillator and load have been employed. Such buffer circuits increase cost and complexity of the equipment in which they are employed. The circuit of the present invention senses excessive load impedance, and turns itself off, protecting both the load and the transistors. In portable equipment, where the load is only connected to the oscillator output intermittently, expensive battery energy may be conserved if the oscillator circuit is shut down when not in use. In other relatively high power applications, such as employed in connection with inductive or dielectric heating, where the work is introduced into the electromagnetic field on an intermittent basis, it is desirable to cause the oscillator to shut itself off when the work is not in position for application of high frequency energy.

SUMMARY OF THE INVENTION

The present invention relates to a novel circuit for protecting a transistor from burnout when employed in an oscillator circuit. A fraction of the load current is fed back in a regenerative fashion to the transistor base. Oscillations of the transistor cease when the load resistance exceeds some critical value. This is due to a reduction in loop gain to less than unity. This automatic shut-off action protects the transistor from the relatively large voltages at the collector that would normally be present during mismatch conditions.

DETAILED DESCRIPTION OF THE PREFERRED EMBODIMENT

Figures 1A, 1B, 2:
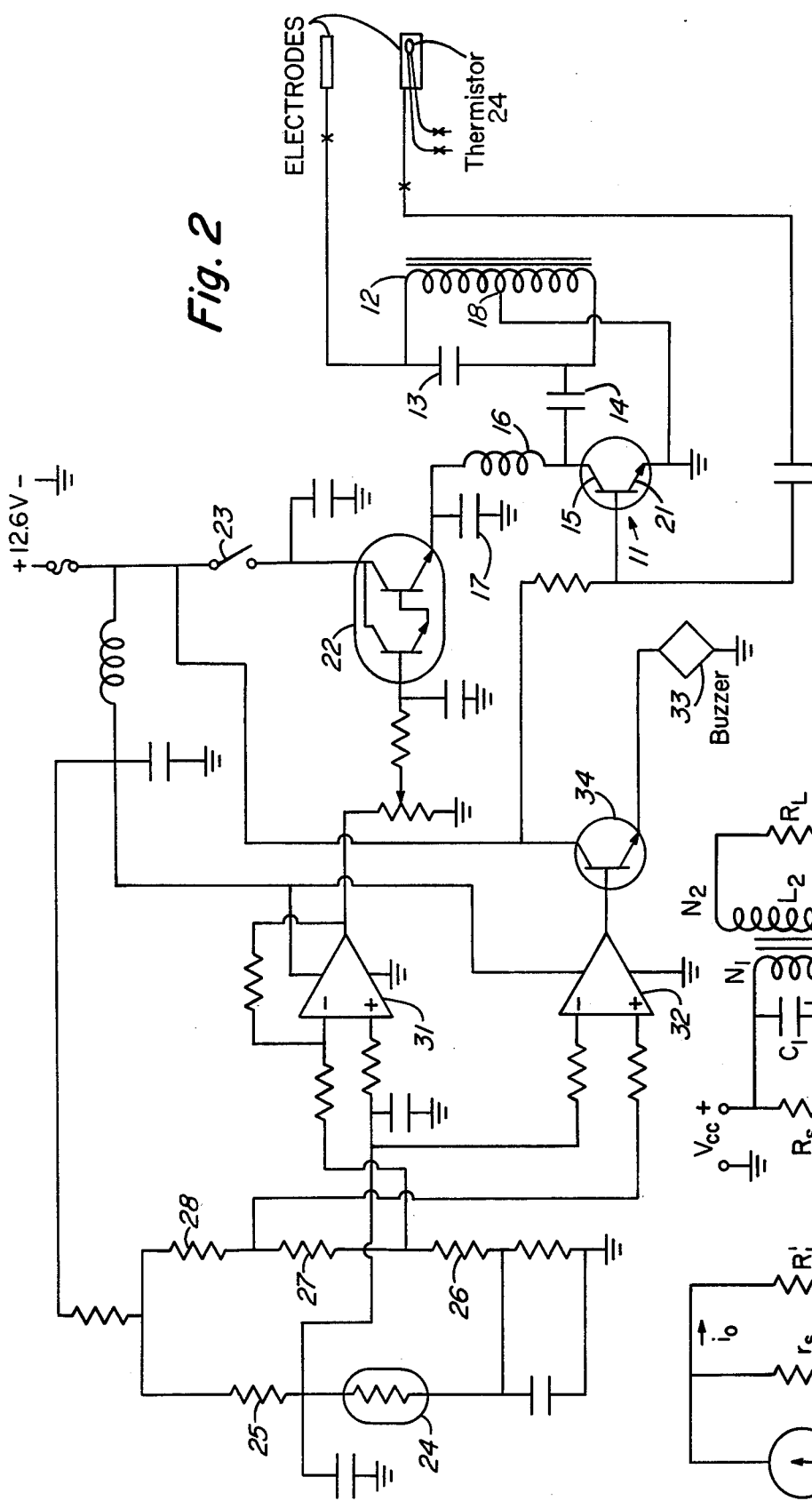
FIGS. 1a and 1b are equivalent circuits for describing the operation of the oscillator of the present invention.
FIG. 2 illustrates an embodiment of the oscillator of the present invention employed in a typical circuit for use in electrosurgery.

Referring now to FIGS. 1a and 1b, simplified equivalent circuits illustrating the mode of operation of the present invention are shown. In the equivalent circuit of FIG. 1a, circulating currents in the resonant circuit are ignored, since only the impedance transformation characteristics of the transformer are relevant to the approximate calculation of loop gain. Further, the collector capacitance of the transistor is ignored. Further approximations include the assumption that load resistance is much greater than the impedance of the base feedback capacitor and the input impedance to the transistor base. In addition, it is assumed that the value of $R_s$ in FIG. 1a is much greater than the absolute value of the reactance of the collector coupling capacitor.

As is well known, frequency of operation is determined primarily by the $L_1C_1$ resonant circuit; that is $$f_r \approx (1/2\pi\sqrt{L_1 \cdot C_1})$$

At this frequency the ratio of collector-current ($i_c$) to base current ($i_b$) is $\beta$, or $i_c = \beta i_b$.

The following relations are defined:

$$R'_L = (N_1/N_2)^2 R_L = R_L/N^2$$

$$N = N_2/N_1$$

$$\alpha = (C_F/C_F + C_s)$$

The following assumptions simplify analysis:
(1) $|X_{cf}| << R_L$
(2) $|X_{cs}| << R_L$
(3) $|X_{L2}| << R_L$
(4) Input impedance at the base of the transistor is small compared to $X_{cf}$ or $X_{cs}$ $$X_c = (1/2\pi fc)$$

$$i_F = i_L(C_F/C_F + C_s) = \alpha i_L$$

$$i_L = (N_1/N_2) i_o$$

$$i_o = \beta i_b r_s / r_s + R'_L,$$

so $$i_L = i_o/N = (N_1/N_2)(\beta i_b r_s / r_s + R'_L)$$

The loop gain is defined as $i_F/i_b$. Then;

$$i_F = (N_1/N_2)(\beta i_b r_s / r_s + R'_L)\alpha$$

$$i_F/i_b = (1/N)(\alpha\beta r_s / r_s + R_L/N_2) = (\alpha\beta r_s / N r_s + R_L/N)$$

For the circuit to oscillate, loop gain must equal or exceed unity; or $$\alpha\beta r_s \geq N r_s + (R_L/N)$$

or $$R_L \leq N(\alpha\beta r_s - N r_s) = N^2 r_s (\alpha\beta/N - 1)$$

or $$R_L \leq N r_s (\alpha\beta - N)$$

The load resistance $R_L$ is matched to the generator when it equals $N^2 r_s$, and maximum power is transferred to $R_L$.

Thus, oscillation will cease when $$R_L > (N_2/N_1)^2 r_s (\alpha\beta N_1/N_2 - 1)$$

Referring now to FIG. 2, a presently preferred embodiment of the present invention is illustrated. The illustrated device is employed for applying rf energy to the eyeball of cattle to kill malignant tumors which occur under certain conditions. This device is portable, operated from a 12-volt battery such as an automobile battery, and is designed to be used by relatively unskilled personnel. The self-protecting oscillator circuit of the present invention includes transistor 11, inductance 12 and capacitor 13, forming a resonant circuit at the desired operating frequency of the oscillator. Collector voltage is applied to collector 15 of transistor 11 through rf choke 16 and bypass capacitor 17. Coupling capacitor 14 connects the LC resonant circuit to collector 15. Emitter 21 of transistor 11 is grounded and connected to the tap on inductance 12.

A Darlington pair 22 is connected to a positive voltage source through switch 23 and serves to control the application of positive voltage to collector 15 of transistor 11 through rf choke 16. The Darlington pair is controlled by a temperature sensing circuit including thermistor 24 and bridge resistors 25, 26, 27 and 28. The thermistor is physically mounted on an electrode of the pair applying the rf field. The thermistor senses the temperature of the body subjected to the rf field. A first differential amplifier 31, connected to the temperature sensing bridge is adjusted to turn off the oscillator transistor 11 through impedance matching Darlington pair 22 at the temperature of 50° C. A second differential amplifier 32, also connected to the temperature sensing bridge, energizes a buzzer 33 through a transistor 34 when a temperature of 48° C. is reached by the thermistor. Buzzer 33 emits a series of buzzes at one second intervals, informing the operator of the approaching 50° C. temperature.

Referring now to the circuit of transistor oscillator 11, rf load current is fed back in a regenerative fashion to the base electrode of transistor 11. Oscillations cease when the load resistance exceeds a critical value due to reduction in loop gain less than unity. Thus, as the electrodes are removed, the impedance between the electrodes increases markedly, cutting off oscillation. This action protects the transistor from the relatively large voltages at the collector that would normally be present during mismatch conditions.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

What I claim is:

1. Apparatus for applying radiofrequency energy to animal tissues comprising:
    an oscillator circuit including a transistor having a base electrode, an emitter electrode, and a collector electrode;
    an inductance and capacitance forming a parallel resonant circuit;
    capacitor means connecting one end of said parallel resonant circuit to said collector electrode;
    a first treatment electrode connected to the second end of said parallel resonant circuit;
    grounding means connecting said emitter electrode and a tap on said inductance;
    a second treatment electrode capacitively connected to said base electrode and providing radiofrequency feedback to said base electrode;
    temperature control means to control the rise in temperature of said animal tissues, said temperature control means including temperature sensing means mounted on one of said treatment electrodes;
    bridge means in circuit with said temperature sensing means; and
    transistor means having a base electrode in circuit with said bridge means and controlling current to said oscillator transistor collector, having a collector electrode connected to a positive current source and an emitter in circuit with said oscillator transistor collector.

* * * * *